United States Patent
Simpson (10) Patent No.: US 6,753,306 B2
(45) Date of Patent: *Jun. 22, 2004

(54) GERMICIDAL AND DISINFECTANT COMPOSITION

(76) Inventor: Joseph J. Simpson, 120 Commandants Way, Chelsea, MA (US) 02150

( * ) Notice: Subject to any disclaimer, the term of this patent is extended or adjusted under 35 U.S.C. 154(b) by 0 days.

This patent is subject to a terminal disclaimer.

(21) Appl. No.: 10/161,400

(22) Filed: Jun. 3, 2002

(65) Prior Publication Data

US 2002/0183229 A1 Dec. 5, 2002

Related U.S. Application Data

(63) Continuation-in-part of application No. 09/469,602, filed on Dec. 21, 1999, now Pat. No. 6,420,332.
(60) Provisional application No. 60/113,830, filed on Dec. 23, 1998.

(51) Int. Cl.$^7$ .......................... C11D 3/386; C11D 1/83; C11D 7/42; C11D 17/00; A47L 13/16
(52) U.S. Cl. ...................... 510/439; 510/295; 510/300; 510/306; 510/320; 510/342; 510/353; 510/356; 510/360; 510/363; 510/421; 510/437; 510/393; 510/438; 510/475; 510/530; 15/209.1; 206/96; 206/77.1; 206/204; 206/37; 8/137; 134/25.2; 134/25.3; 134/25.4; 134/39; 134/42
(58) Field of Search ................................. 510/295, 300, 510/306, 320, 342, 353, 356, 360, 363, 421, 437, 393, 438, 439, 475, 530; 15/209.1; 206/96, 77.1, 204, 37; 8/137; 134/25.2, 25.3, 25.4, 39, 42

(56) References Cited

U.S. PATENT DOCUMENTS

| | | | |
|---|---|---|---|
| 3,819,528 A | * 6/1974 | Berry | 252/153 |
| 4,243,546 A | 1/1981 | Shaer | 252/174.12 |
| 4,287,082 A | 9/1981 | Tolfo et al. | 252/174.12 |
| 4,305,837 A | 12/1981 | Kaminsky et al. | 252/174.12 |
| 4,537,707 A | * 8/1985 | Severson, Jr. | 252/545 |
| 4,561,991 A | * 12/1985 | Herbots et al. | 252/118 |
| 4,998,984 A | * 3/1991 | McClendon | 206/205 |
| 5,030,378 A | * 7/1991 | Venegas | 252/174.12 |
| 5,422,030 A | * 6/1995 | Panandiker et al. | 252/135 |
| 5,501,820 A | 3/1996 | van den Bergh et al. | 252/549 |
| D387,704 S | * 12/1997 | Berti | D4/114 |
| 5,773,405 A | 6/1998 | Bruhnke | 510/519 |
| 5,840,675 A | * 11/1998 | Yeazell | 510/439 |
| 5,851,973 A | 12/1998 | Foley | 510/235 |
| 5,990,065 A | * 11/1999 | Vinson et al. | 510/237 |
| 6,013,614 A | * 1/2000 | Mahdessian | 510/277 |
| 6,420,332 B1 | * 7/2002 | Simpson | 510/439 |

FOREIGN PATENT DOCUMENTS

| | | | | |
|---|---|---|---|---|
| EP | 0611206 A2 | | 2/1994 | C11D/17/00 |
| EP | WO 97/29178 | * | 8/1997 | C11D/17/04 |
| WO | WO 98/28392 | * | 7/1998 | C11D/3/30 |
| WO | WO 00/37602 | | 6/2000 | C11D/3/386 |

OTHER PUBLICATIONS

Simpson, J., U.S. patent application Ser. No. 09/469,602, "A Blood and Organic Stain Remover," filed Dec. 21, 1999 (see WO 00/37602).

* cited by examiner

*Primary Examiner*—Brian P. Mruk
(74) *Attorney, Agent, or Firm*—Perkins Smith & Cohen, LLP; Jacob N. Erlich (57) ABSTRACT

A germicide and disinfectant composition contains detergent and at least two enzymes adapted to cause lysis in glycoprotein in infectious agents. These germicidal and disinfectant compositions are used in conjunction with prepackaged wipes and kits that allows the user to remove liquid or dried contaminated material without coming into direct contact with the contaminated material.

81 Claims, 7 Drawing Sheets

GERMICIDAL AND DISINFECTANT COMPOSITION

CROSS REFERENCE TO RELATED APPLICATIONS

This application is a continuation-in-part application of U.S. Ser. No. 09/469,602 titled "A Blood and Organic Stain Remover" that was filed on Dec. 21, 1999 now U.S. Pat. No. 6,420,332, which application claims priority from U.S. provisional application S No. 60/113,830, filed Dec. 23, 1998.

FIELD OF THE INVENTION

The instant invention relates to the field of germicidal and disinfectant compositions. These germicidal and disinfectant compositions are used in conjunction with prepackaged wipes and kits.

BACKGROUND OF THE INVENTION

Blood and other bodily fluids (e.g. urine, feces, vomit) contain various infectious agents, including bacteria and viruses. Similarly, interior and exterior body surfaces, including most prominently mucous membranes, also have various infectious agents on their surfaces. Thus, in a variety of disaster, emergency, and non-emergency situations, where exposure to these contaminated fluids and surfaces can occur, there is a need to neutralize and remove these infectious agents with effective germicides in order to prevent secondary infection of a variety of individuals, including medical and emergency response personnel as well as family, friends, and other bystanders.

Due to the increased numbers of individuals potentially harboring these infectious agents, there is a growing concern among emergency response teams, military and civilian medical and dental staff, law enforcement personnel and, more recently, even travel and tourist personnel, educators, and co-workers over the possibility of coming in contact with a variety of infectious agents, including human immunodeficiency virus (HIV), hepatitis, and, more recently, anthrax and smallpox. Examples of their concern would include, but not be limited to, the exposure that they experience in classrooms, athletic departments, the industrial workplace, hotels and motel suites, patrol cars, emergency response vehicles and public transportation. In addition, their concern and that of public health officials is heightened by the long-term viability of some of these infectious agents, such as hepatitis, and the lack of effective vaccines against some of these infectious agents, such as anthrax.

These concerns are not unfounded. While in a given population the presence of HIV and hepatitis is statistically extremely remote, in a gathering where the potential for a high incidence of these viruses is present, there is justification to be concerned. For instance, a chartered cruise ship or aircraft, a convention or rally held at a hotel or motel containing several thousand guests known to potentially be carriers of this virus. In the case of law enforcement, the persons involved would suggest a significant increase in the probability for encountering these viruses.

Germicides and disinfectants are a standard part of the arsenal used to combat these infectious agents. However, detergent formulations alone have been at best only moderately successful in killing germs and disinfecting fluids and surfaces. Addition of enzymes that can inactivate or kill germs can improve the effectiveness of these germicidal and disinfectant compositions. However, enzyme-containing compositions have known problems. Separation of the different components of an aqueous composition containing an enzyme or enzymes into different layers or phases (termed phase separation) and a resulting decrease in germicidal and disinfectant capacity is known to occur.

Additionally, since enzymes themselves are proteins, they can digest each other. Further, enzymes must maintain a certain chemical configuration or shape in order to remain active. A change to that configuration which results in inactivation is called denaturation. Heat, unfavorable pH, and other such conditions may result in denaturation or partial denaturation of enzymes present in a germicidal and disinfectant composition, thus decreasing the shelf-life of the composition or at least rendering it less effective with time. Thus, formulating an effective germicidal and disinfectant composition containing enzymes that remains phase stable and that maintains enzymatic activity has proven difficult. Further, many such compositions contain phosphates and other chemicals that can pollute the environment.

Various patents have proposed ways to stabilize single enzyme type detergent compositions that can potentially act as germicides and disinfectants. U.S. Pat. No. 3,819,528 provides an aqueous enzyme composition wherein the enzyme is an amylase. A water-soluble calcium salt, and an organic stabilizing agent such as 1,3-propanediol or an aliphatic glycol are illustrated as stabilizers. U.S. Pat. No. 4,287,082 discloses a homogeneous proteolytic enzyme-containing liquid detergent composition containing saturated fatty acids. U.S. Pat. No. 5,422,030 provides liquid detergents with an aromatic borate ester to inhibit proteolytic enzyme degradation of the enzymes in the composition.

SUMMARY OF THE INVENTION

The instant invention provides a liquid germicide and disinfectant composition that contains detergent and at least two enzymes, an enzyme stabilizing system a detergent and water. The composition is adapted to cause lysis of glycoprotein in infectious agents. Such agents can include viruses such as HIV, smallpox and all forms of hepatitis, including the extremely dangerous hepatitis C. Methods for using the germicide and disinfectant composition as are also provided. The composition may be incorporated into a pre-moistened prepackaged wiper that allows the user to remove liquid or dried contaminated material without coming into direct contact with the contaminated material. The composition, with or without its prepackaged wiper, may be incorporated into a potentially disposable kit that is designed to decontaminate fluids and surfaces containing germs and infectious agents, thus allowing the user to remove liquid or dried contaminated material without coming into direct contact with the contaminated material. The composition may be provided in a re-sealable bag for both pre-use storage and disposal. Such bag may be everted to form a mitt.

DETAILED DESCRIPTION OF THE INVENTION

In accordance with the present invention, it has been found that by combining a nonionic surfactant or a mixture of nonionic and anionic surfactants, a protease or a mixture of a protease and an amylase, and a stabilizing system, effective germicidal and disinfectant enzymatic activity in an aqueous detergent solution may be maintained for prolonged periods of time.

In the inventive germicidal and disinfectant composition, water comprises up to 50% by weight of the total composition. The amount of water present will vary depending upon the other solvents needed to dissolve certain components of the formulation(s) and/or to clarify the liquid composition. The preferred amount of water is from about 40% to about 60%.

Organic Synthetic Surface-Active Agents:

The preferred organic synthetic surface-active agents are biodegradable and are nonionic surfactants, anioinic surfactants, or mixtures of nonionic and anionic surfactants.

The nonionic surfactants that are suitable are ethoxylated fatty alcohols and ethoxylated fatty acids. Sulfonates and succinates may also be useful. Ethoxylates are produced by condensing ethylene oxide with a hydrocarbon having a reactive hydrogen atom in the presence of an acid or base catalyst. Such surfactants can be represented by the generic formula $RA(CH_2 CH_2O)_nH$ wherein R represents the hydrophobic moiety, A represents the group carrying the reactive hydrogen atom and n represents the group average number of ethylene oxide moieties. R typically contains about 8 to 22 carbon atoms, and n usually varies from about 2 to about 10, and preferably from about 2 to about 8 groups/mole, avg. The hydrophile/lipophile balance number (HLB) is preferably between about 3 to about 15. Preferred ethoxylated fatty alcohols nonionic surfactants include Neodol$^R$ 23-6.5 and Neodol$^R$ 25-3 (each available from Shell Chemical Co.; Parsippany, N.J.).

Anionic surfactants can be represented by the general formula RSOM wherein R represents a hydrocarbon selected from the group consisting of straight or branched alkyl radicals containing from about 8 to about 24 carbon atoms. M is a salt forming cation that typically is selected from the group consisting of sodium, potassium, ammonium and derivatives thereof. The preferred anionic surfactant is a simple salt such as for example, sodium laureth sulfate (available from Stepan Co., Northfield, Ill.).

The Enzymes:

Enyzmes that are useful in the present invention comprise proteases and alpha-amylases. The proteases are typically derived from bacterial sources and are preferably active in a pH range of about 4 to about 10. The preferred pH range is neutral to somewhat basic, from about a pH of 6.8 to about a pH of 9. A protease can break the peptide bonds of proteins found in blood and other fluids, including contaminating infectious germs. This results in short chain molecules having free amino and carboxy groups, ionic groups that are more easily washed away with water and/or detergent. Breaking the peptide bonds also results in lysis of the glycoprotein and a disruption of the microbe's cellular mechanics. It is preferred that the protease be able to function at high temperatures (up to about 90 degrees C.) as well as at room temperature. An example of such a protease is Savinase$^R$ 16L which is available from Novo Nordisk BioChem North America, Inc., Franklinton, N.C.

An amylase is an enzyme that catalyzes a reaction that breaks starch molecules into shorter chain molecules making the removal of the starch with water and/or detergent easier. Starches may enhance the adherence of proteins to fibers and hard surfaces. The preferred amylase is able to function at high temperatures (up to about 90 degrees C) as well as at room temperature. Preferably, the amylase can function at a pH from about 6.8 to about 11.5. An example of an amylase is Termamyl$^R$ 300L which is available from Novo Nordisk BioChem North America, Inc., Franklinton, N.C.

Optionally, an enzyme that facilitates the breakdown of fats and oils into shorter chain molecules may be added to the spot remover. Such an enzyme is a lipase such as for example, Lipolase$^R$ which is available from Novo Nordisk BioChem North America, Inc., Franklinton, N.C. Fats and oils may enhance adherence of other organic molecules. By combining a lipase, a protease, and optionally, an amylase in an aqueous detergent solution, the types and variety of macromolecules from germs and infectious agents that can be neutralized may be unexpectedly improved.

In the preferred germicide and disinfectant composition, an amylase and a protease are present at a concentration of at least about 0.1% w/w.

The Enzyme Activity Stabilizers:

Useful enzyme activity stabilizers include compounds that provide a source of free calcium in the solution such as for example calcium salts; alkyl or branched alcohols such as for example ethanol and isopropyl alcohol; alkanolamines such as for example triethanolamine and acids preferably organic acids; and mixtures of petroleum distillates.

Up to 25% by weight of alcohol may be added to the spot remover. Preferably between 1 to 15% by weight of alcohol are added. Petroleum distillates such as for example mineral spirits may be added in amounts of up to 75% by weight with less than 25% being preferred.

The pH of the spot remover may be adjusted by adding an acid or a base to achieve the preferred pH which is from about 6.8 to 8.5. Alkanolamines such as for example triethanolamine, may be added to make the solution more basic. Acids or salts of acids may be added to adjust the pH towards a lower pH. Useful carboxylic acid salt includes acetates and propionates. The preferred salt is sodium formate.

Unsaturated fatty acids may also be added such as for example oleic acid. Such fatty acids may serve a dual function by enhancing cleaning power and altering pH. To obtain the germicidal and disinfectant composition, all ingredients are dissolved and mixed together. The final volume is adjusted with distilled water (DI).

The following examples illustrate the invention:

EXAMPLE 1

The following illustrate the compositions of the present invention. Preparation of the following Formulae is achieved by solubilizing, clarifying and mixing the components. All parts, percentages, and ratios used herein are by weight unless otherwise specified.

| Formula A | |
|---|---|
| calcium chloride | 0.05% |
| sodium formate | 2% |
| triethanolamine | 1% |
| ethanol | 5% |
| Neodol<sup>R</sup> 23-6.5 | 30% |
| Steol<sup>R</sup> CS-460 | 20% |
| enzymes | 0.2–3% |
| DI water | to 100% |
| Formula B | |
| Neodol<sup>R</sup> 25-3 | 10% |
| Neodol<sup>R</sup> 23-6.5 | 10% |
| mineral spirits | 20% |
| isopropanol | 12% |
| triethanolamine | about 1.2% |
| oleic acid | about 2.3% |
| calcium chloride | 0.05% |
| sodium formate | 2% |
| enzymes | 0.2–3% |
| DI water | to 100% |

Enzymes: Savinase$^R$ 16 L, Lipolase$^R$ 100 L, and Termamyl$^R$ 300 L.

EXAMPLE 2

The effectiveness of Formula A and Formula B at removing dried fluids was tested with and without added enzymes on standardized swatches having the following compositions: I—blood, milk, carbon ink on 100% cotton (100%); II—blood, milk, carbon ink on polyester-cotton; III—cocoa and milk on 100% cotton; IV—maize starch and carbon ink on 100% cotton. Swatches I and II were observed for protease activity. Swatches III and IV were observed for amylase activity. Lipolase$^R$ 100L was observed to separate out of each of Formulae A and B.

On a weight/weight basis, equal amounts of each of Savinase$^R$ 16L, Lipolase$^R$ 100L, and Termamyl$^R$ 300L were tested in Formulae A and B at concentrations ranging from 0 to 0.5%. One milliliter aliquots of the respective Formulae were rubbed for 10 seconds into the dried fluid on each of the standardized swatches. The standardized swatches were allowed to soak for 5 minutes and then were rinsed in tap water for 5 minutes. A refractometer (US Testing Co., Model 7243S) was used to provide reflectance measurements.

Figure 1:
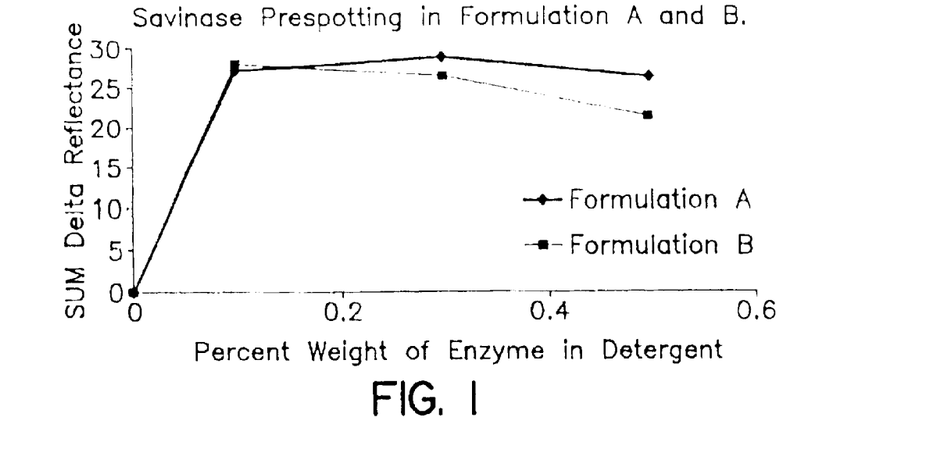
FIG. 1 illustrates the ability of Formula A and Formula B to remove material containing protein as measured by reflectance.
Figure 2:
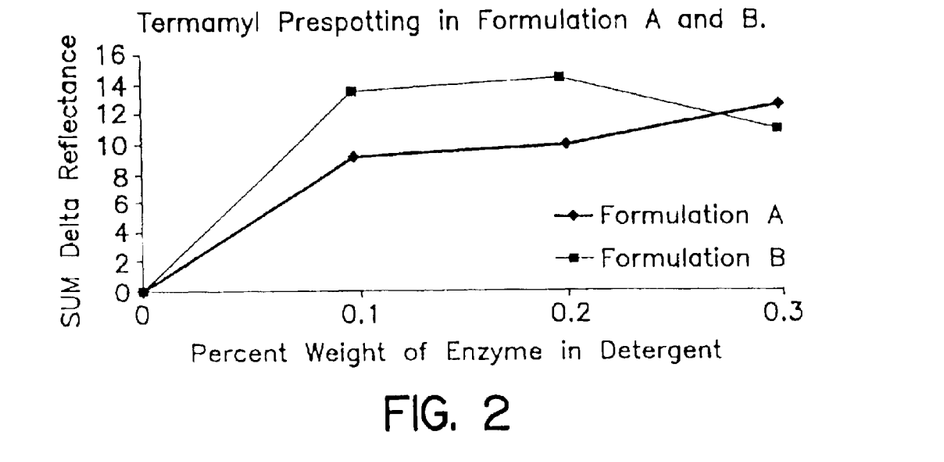
FIG. 2 illustrates the ability of Formula A and Formula B to remove material containing starch as measured by reflectance.

The results shown in FIG. 1 for protease activity and in FIG. 2 for protease/amylase activity, demonstrate that while the detergent composition alone was effective at removing dried fluids, addition of the protease and the amylase greatly enhanced dried fluid removal even at concentrations as low as 0.1% w/w.

EXAMPLE 3

Figure 3A:
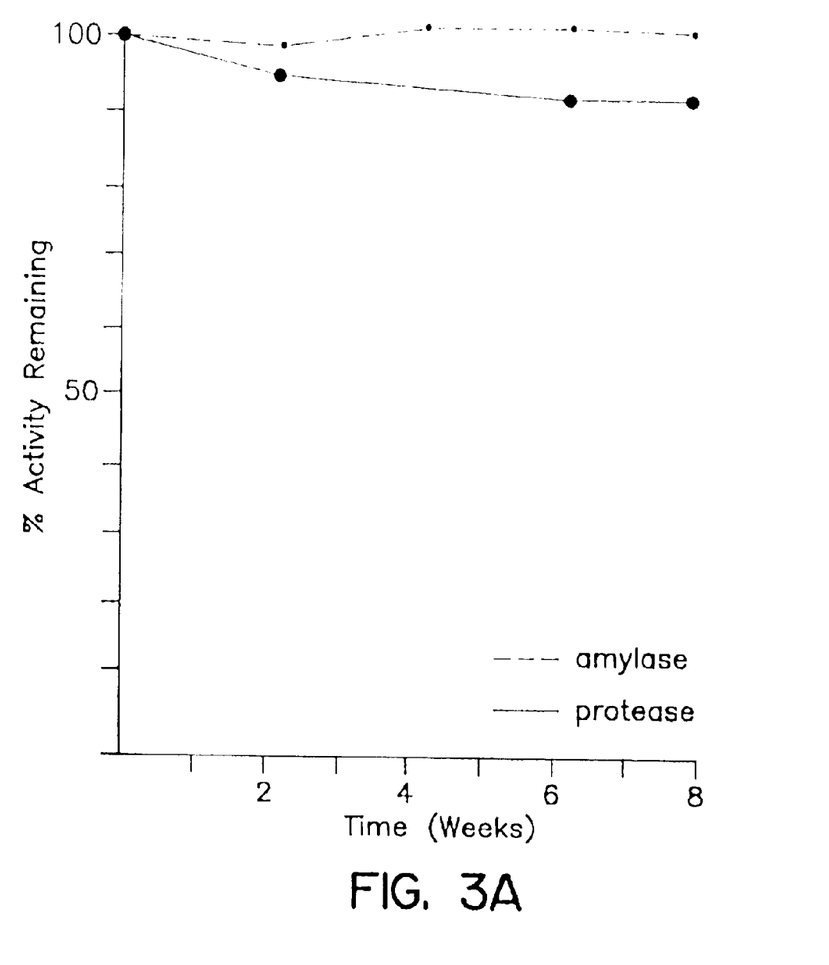
FIG. 3A illustrates the stability of Formula A with time as determined by the enzymatic activity therein.
Figure 3B:
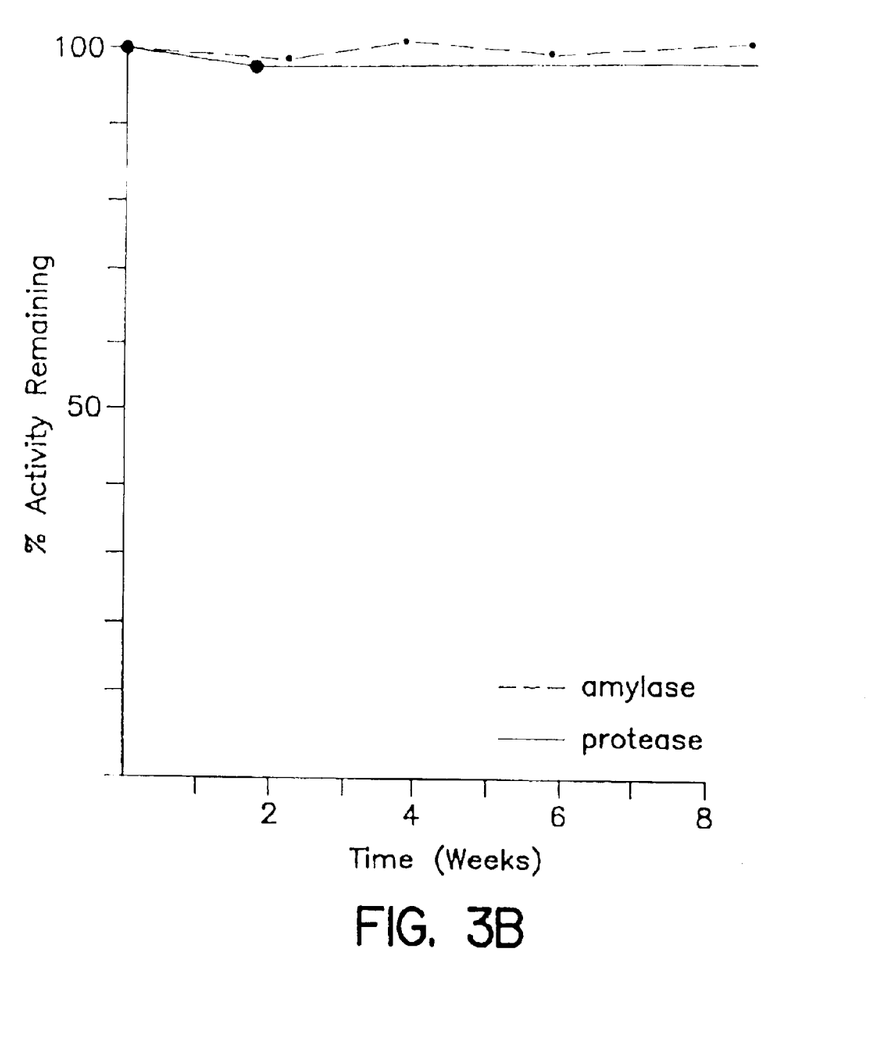
FIG. 3B illustrates the stability of Formula B with time as determined by the enzymatic activity therein.

Storage stability of Formulae A and B when 1% each of Savinase$^R$ 16L, Lipolase$^R$ 100L, and Termamyl$^R$ 300L were present in the aqueous detergent composition was determined using a standard accelerated stability test. An eight week incubation at an elevated temperature of 30 degrees C. was performed wherein enzymatic activity was determined at two week intervals. Each formulation was incubated in sealed glass vials in an incubation chamber (VWR Scientific Laboratories, Inc., Model #535). Enzymatic activity of the protease, amylase, and lipase was determined using a spectrophotometer (Carey, Inc., Model 3C) and protein or starch standards. Wash performance evaluation was performed using a terg-o-tometer (United States Testing Co., Inc.; 7243S). Results of the wash test were evaluated using a Hunter Labscan reflectometer (SN/13859). FIG. 3A illustrates protease stability with time in Formulae A and B. FIG. 3B illustrates amylase activity with time in Formulae A and B. It can be seen that both enzymes in both formulae retain greater than 90% activity with time.

The present invention is useful for disinfecting and decontaminating fresh and dried blood and related bodily fluids. Using these germicidal and disinfectant compositions, direct skin contact with infectious agents and contamination may be prevented so that transmission of germs and the resultant secondary infection is reduced or eliminated. These compositions are designed to reduce the infectivity of a variety of viral infective agents, including, but not limited to, HIV, the longer lived hepatitis viruses such as the very dangerous hepatitis C, and smallpox. These particular viruses are a major public health concern given the seriousness of the consequences of infection and the fact that vaccines do not currently exist, or are in short supply, for these viruses. Similarly, these compositions can reduce the infectivity of a variety of bacterial infective agents, including, but not limited to, the more recently important anthrax bacteria by means of their cleansing activity.

The inventive germicidal and disinfectant compositions find use in medical- and dental-related facilities, such as medical offices, hospitals, home health care, nursing care facilities, and ambulances, as well as in quasi-medical facilities such as beauty and hair salons. They can also be used in law enforcement tasks and centers as well as fire stations and related fire emergencies and their locations. Additionally, they can be used in the travel and tourist industry, including lodging establishments, aircraft, and cruise ships. Yet another example of locations in which these inventive compositions can be used is schools and related athletic and nursing facilities. And generally, these compositions can be used in a variety of custodial and janitorial settings. In short, these germicidal and disinfectant compositions can be used in any setting in which decontamination is required. The growing concern of individuals employed in these settings and facilities that they will contract various infections from fresh or dried blood and bodily fluids present in emergency and other situations makes the use of the inventive germicidal and disinfectant compositions imperative in these settings.

In addition to being used on blood and other bodily fluids directly, these germicidal and disinfectant compositions can be used on any contaminated surface. These may include medical, surgical, and dental devices as well as any contaminated surface, such as tables, chairs, and counter-tops. An example of the use of these germicidal and disinfectant compositions would be in the pre-sterilization cleaning of flexible fiberoptic endoscopes which is necessary to remove potentially contaminated tissue-related materials before sterilization, which may serve to harden these materials onto the instrument. Other instruments and surfaces may be treated in a similar fashion to achieve germ inactivation and disinfection.

The method of the present invention for treating fresh and dried blood and bodily fluids would generally include contacting the fresh and dried blood and bodily fluids with a germicidal and disinfectant composition adapted to cause lysis of glycoprotein in infectious agents, absorbing the germicidal and disinfectant composition along with the fresh and dried blood and bodily fluids by using absorbent wipe material, and disposing of the absorbent wipe material containing absorbed germicidal and disinfectant composition and fresh and dried blood and bodily fluids. Variations to this process would depend upon the physical applicator and packaging.

Figure 4:
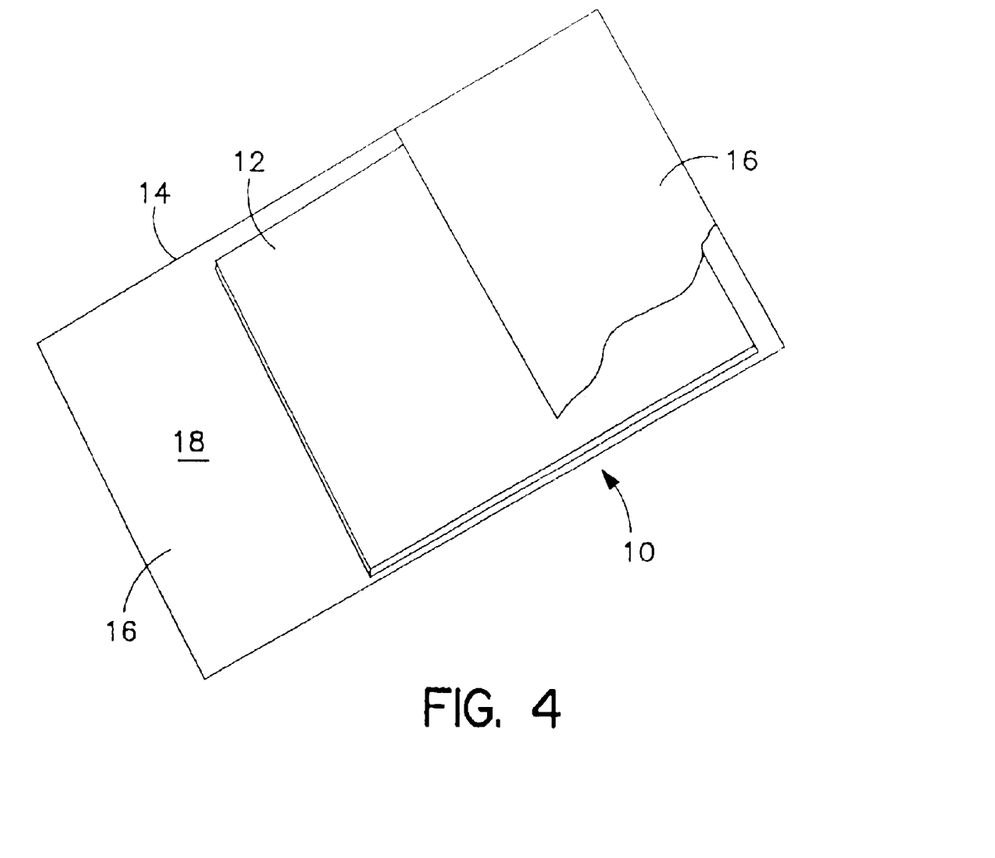
FIG. 4 illustrates one embodiment of the prepackaged germicide and disinfectant composition of this invention.

The present inventive compositions may also be incorporated into prepackaged disposable wipers 10, for example such as illustrated in U.S. Pat. No. 4,998,984, the disclosure of which is incorporated herein by reference. The package may have an absorbent material wipe 12 attached to and enclosed in a metal foil package 14 provided with fold back flaps 16. The inventive composition selected from Formulae A or B can be placed on the absorbent material prior to packaging. Alternatively, the inventive composition may be sprayed or poured onto the absorbent material. The fold-back flaps may be used to form a handle 18 for the wipe to clean up the fresh or dried blood or bodily fluid. After contacting the fresh or dried blood or bodily fluid spot with the wipe and removing it, the flaps may be folded over the used wipe without the need for direct skin contact with the wipe. Additionally, the user may remove fresh or dried blood or bodily fluids with the inventive compositions by protecting the skin through use of gloves.

Alternate methods of packaging the invention composition which allow use without the need for direct skin contact with the fresh or dried blood or bodily fluid or the inventive composition are contemplated. In overall concept, the packaging is designed to allow unitary construction wherein the package can be easily disposed of once used in a way that avoids contact with and contamination by the germs present. As another example, this can be accomplished by the use of an envelope or bag like apparatus which works as a pre-use storage container and a re-sealable, post-use disposal container. In a preferred embodiment, the bag or envelope is first everted to expose an absorbent wipe for usage. After usage, the bag is un-everted for disposal. These examples are discussed in greater detail in reference to FIGS. 5–7.

The inventive germicidal and disinfectant composition can also be provided as a clean-up kit as described below in reference to FIG. 8.

The absorbent material used in the prepackaged wipes of this invention can be made of any suitable material. In general, the material used should be hydrophobic and able to absorb a large amount of the inventive germicidal and disinfectant compositions without leaking significant amounts of the liquid. Such materials are commonly available and typically include a mixture of approximately 40% polypropylene and 60% cellulose. Such materials that can hold up to 20 times their weight in liquid without dripping and can soak up approximately 30 times their weight in liquid. However, the absorbent material used does not necessarily need to be saturated with the present composition. Depending on the task it is being used for, the material may be less than fully saturated with the inventive composition. Being less than fully saturated will be of most importance when liquid contamination is being cleaned. Alternatively, a more saturated absorbent material will be more useful on dried contamination.

Figure 5:
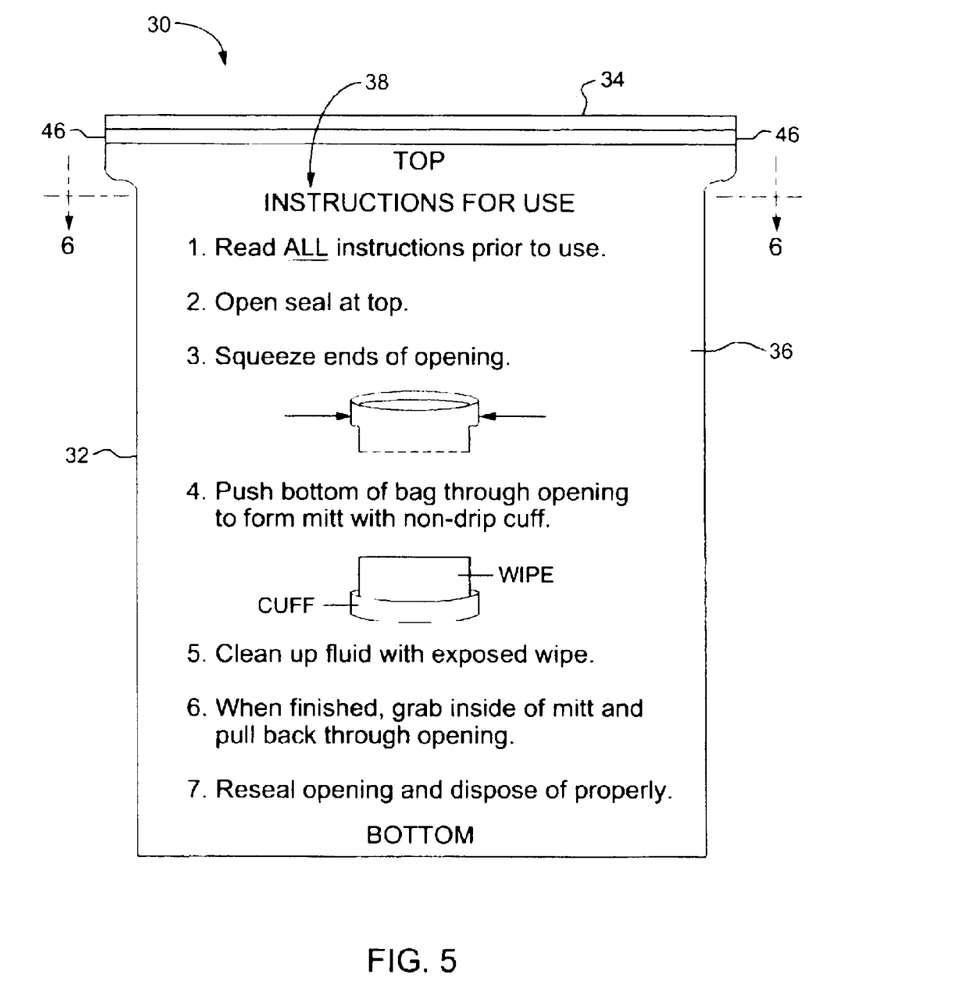
FIG. 5 is a front view of a device constructed in accordance with another embodiment of the present invention.

FIG. 5 shows a front view of a packaged mitt 30 constructed in accordance with an embodiment of the present invention. Mitt 30 is embodied in a plastic bag 32 having a re-sealable opening 34. Any suitable material may be used for bag 32 which provides an impenetrable barrier to the germicidal and disinfectant composition as well as any contaminants and fluids to be retrieved. Such materials are water proof and typically acid resistant.

Plastic bag 32 is flat and includes two opposing sides, with at least one outside surface 36 having instructions 38 printed there upon for proper use of mitt 30. Instructions 38 are oriented so that the re-sealable opening 34 is located along the top edge of mitt 30, which orientation will be shown to facilitate proper usage of mitt 30. The use of bag 32 provides significant advantages to the present embodiment. Most importantly, bag 32 is used as a storage container for the liquid active ingredients of the germicidal and disinfectant composition described above. Further, locating the absorbent material inside bag 32 frees the entire outside of bag 32 for the printing of instructions for proper usage. This added surface area for printing instructions provides room for either more instructions or larger print instructions thereby improving the safety of using mitt 30. Re-sealable opening 34 may be formed by any commonly available re-sealable, plastic bag closure.

Figure 6:
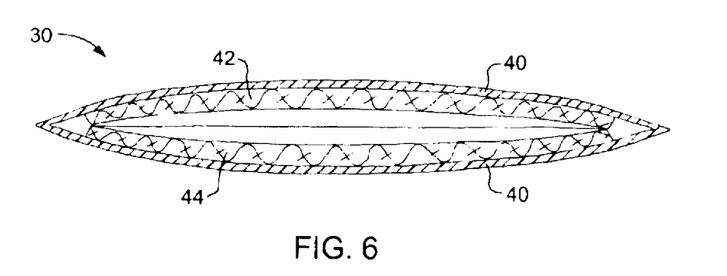
FIG. 6 is a cross sectional view of the device of FIG. 5 taken along view lines 6—6 of FIG. 5.

FIG. 6 shows a cross-section view of bag 32 taken along view lines 6—6. FIG. 6 shows the opposed flat sides 40 of mitt 30 as well as two flat absorbent material layers 42, 44, located within bag 32. To facilitate use of the germicidal and disinfectant composition, only a single layer 42 of absorbent material is necessary. The presence of two absorbent material layers 42, 44 is an enhanced embodiment which is enabled by the use of bag 32. Using two absorbent material layers provides mitt 30 with greater capacity for both the germicidal and disinfectant composition described above as well as the amount of spilled contaminated fluid that can be captured.

The increased amount of absorbent material also allows flexibility in the type of material used such that mitt 30 may be provided with a softer and more absorbent layer along with a coarser more abrasive portion for cleaning stubborn material such as dried blood.

Figure 7:
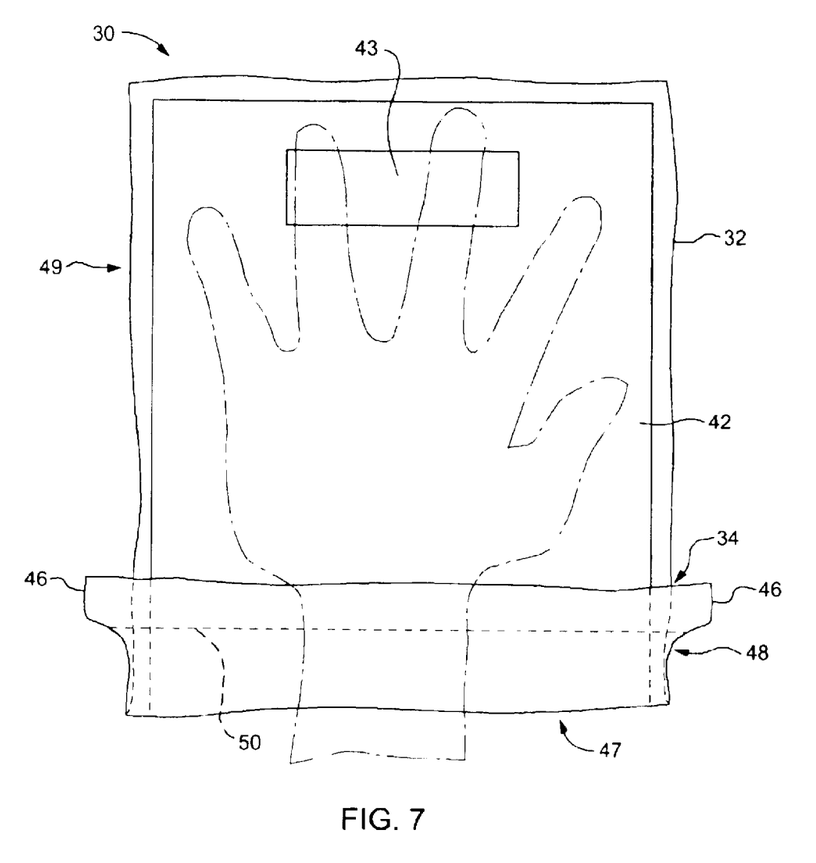
FIG. 7 is side view of the device of FIG. 5 shown in appropriate position for usage.

As mentioned, exterior surface 36 of the packaged mitt 30 includes instructions 38 for the proper use of mitt 30. The packaged mitt 30 is oriented so that emergency or other personnel would pick up the plastic bag 32 and read the instructions printed thereof, automatically orienting the re-sealable opening 34 in an upward direction. After opening the re-sealable opening 34, such personnel would be instructed to squeeze opposing ends 46 of opening 34 thereby creating space between opposite sides of opening 34. Personnel are then instructed to push the bottom of bag 32 through opening 34 to thereby partially evert bag 32 and create the useable mitt 30 of the present embodiment as shown in FIG. 7. Of course, the first instruction would advise users to read all instructions prior to everting bag 32. To facilitate eversion of bag 32, the sides of opening 34 may be made of stiffer or heavier gauge material than the remainder of bag 32. The bottom of bag 32 may also be pleated for this purpose.

FIG. 7 shows a side view of mitt 30 properly oriented for use in cleaning up contaminated liquids. In accordance with the user instructions, mitt 30 is only partially everted, or turned inside out, so that the opening 34 thereby forms a non-drip cuff 48 around the entire periphery of the opening 47 and absorbent material layers, 42, 44. Mitt 30 may then be used by insertion of a hand through opening 47 into the everted interior of mitt32. For this purpose, mitt 30 and bag 32 are sized with an appropriate width to just accommodate the largest typical human hand without spreading fingers. In this manner, smaller human hands can be used in the same mitt 30 by using spread fingers and thereby providing adequate control thereof during usage. Further to this end, the exterior surface, such as 36 of bag 32, may be made with a high coefficient of friction.

It should be noted that cuff 48 is lined with absorbent material up to the phantom line 50. In this manner, cuff 48 further forms a reservoir for excess liquid, which reservoir does not allow for uncontrolled pooling of that excess liquid. Instead, the liquid runs into cuff 48 through absorbent material layer 42 on the interior surface of bag 32, and such liquid is distributed throughout the area of cuff 48 within two lawyers of absorbent material located on either surface of the cuff below phantom line 50. This reservoir function allows the absorbent material to perform close to its highest absorbent capacity while still containing all of the liquid.

To facilitate the formation of cuff 48 with an enhanced reservoir capability, mitt 30 is constructed to be elongated in the direction orthogonal to, or normal to opening 34. This arrangement further enables a user to adjust the amount of absorbent material 42 which is exposed, above opening 34 in FIG. 7, relative to the size of cuff 48, depending upon the nature of the contaminated fluids to be captured. In the event of a large amount of fluid, personnel may form mitt 30 with a more limited exposed portion of absorbent layer 42 and a relatively enlarged cuff 48. In the case of limited or partially dried contaminated fluids, personnel may increase the exposed area of absorbent layer 42 and correspondingly decrease the size of cuff 48. In yet another variation, a larger area of absorbent layer 42 may be used to during scrubbing of a contaminated surface or material and then the size of cuff 48 may be expanded to allow for the removal of fluid resulting from the scrubbing. In accordance with one variation, absorbent layers 42, 44 may be highly saturated with the germicidal and disinfectant composition, which is first expelled from absorbent layer 42 on to the surface to be cleaned, thereby allowing a soaking action, and then the expelled fluid may be retrieved back into the absorbent material layer 42.

To further facilitate the functioning of bag 32 to form mitt 30 and the functionality of cuff 48, the re-sealable opening 34 is made larger than the width of the bag portion 49 as shown in FIG. 7.

Once a user is finished with cleanup, the ends 46 of opening 34 are slightly squeezed while the user grabs the interior of mitt 30 and pulls the exposed end back through opening 34. In this manner any excess fluid located in cuff 48 is readily retained within bag 32. The bag may then be resealed and properly disposed of.

FIG. 7 also demonstrates the flexibility enabled by the use of two absorbent material layers 42, 44. A portion 43 of absorbent material layer 42 is shown and may be constructed with a coarser, more abrasive type of absorbent material. Thus, the functionality of coarse scrubbing is added to the disposable wiper without significantly sacrificing the absorbent capacity thereof.

The design of bag 32 is thus multi-functional as it provides a sealed storage container for the germicidal and disinfectant composition described above, a useable cleaning mitt 30 with non-drip cuff 48, and a sealable disposal container for contaminated fluids.

The present invention is not intended to be limited to the physical form described in reference to FIGS. 5–7. Any suitable delivery system may be used, such as a simple sponge form of absorbent material, which may be provided in a re-sealable container capable of serving as both an initial storage container and a subsequent disposal container.

Figure 8:
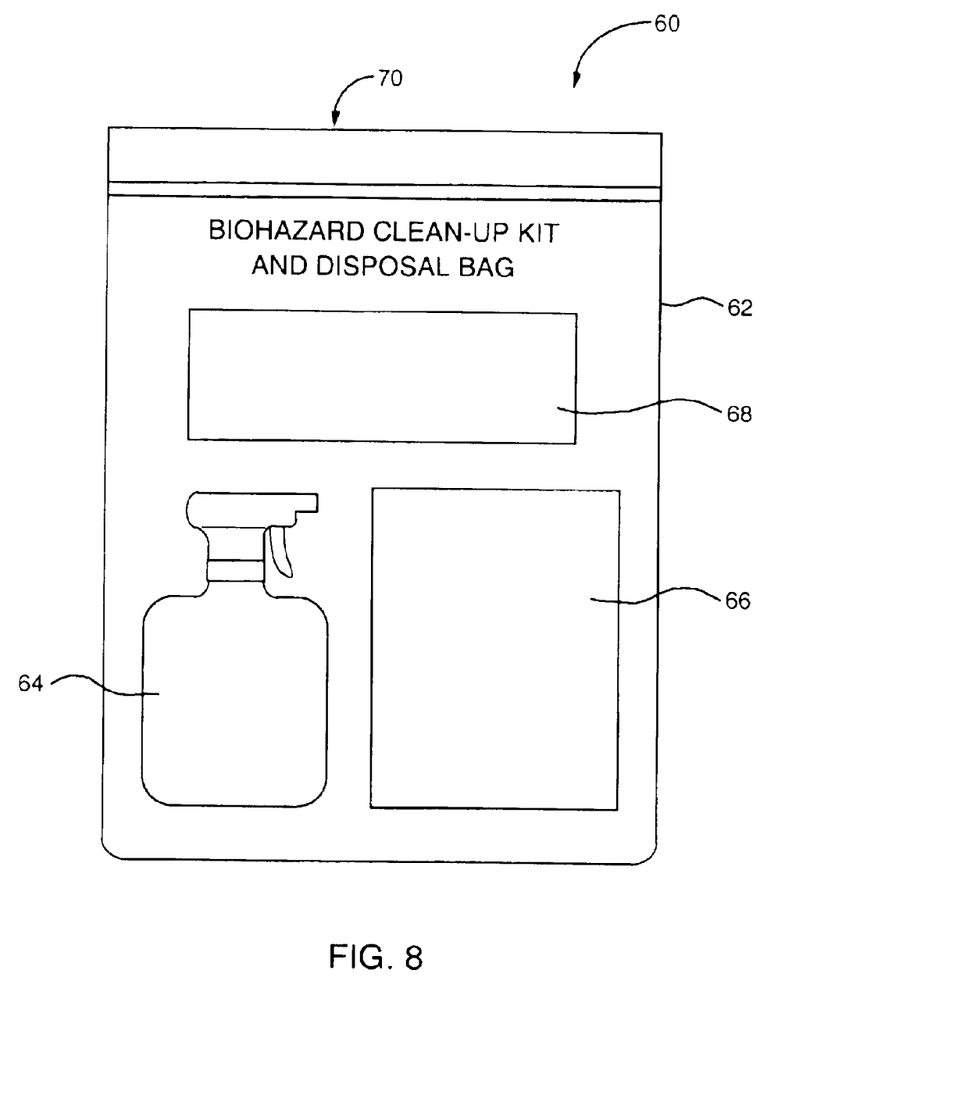
FIG. 8 is a representational depiction of a biohazard clean-up kit constructed in accordance with another embodiment of the present invention.

FIG. 8 is a representational depiction of a biohazard clean-up kit 60. Kit 60 generally includes a storage container 62, the germicidal and disinfectant composition described above stored in a sealed, dispensing container 64, a disposable material wipe 66, and addition biohazard protective equipment such as gloves or a biohazard disposal bag.

Storage container 62 may include a re-sealable opening 70 and thereby serve a second function as a biohazard disposal bag. Dispensing container 62 may take any suitable form such as a spray or pour top container, or even a plastic bag with a tear-off top. Disposable material wipe 66 may also take any suitable form such as that described for the absorbent layer 42 of FIGS. 5–7, including multiple pieces thereof. Storage container 62 may optionally be made of clear plastic and may include instructions for use in the same manner as bag 32 of FIG. 5.

It can be readily appreciated that the applications described herein for use of the germicidal and disinfectant composition not only enable use of the composition for viral infectious agents but also provide a protective cleansing function for use on any similar form of infectious agents. The effect of the inventions described herein is to thereby reduce secondary infections from such other infectious agents, including bacterial agents such as anthrax.

The foregoing is considered only illustrative of the currently preferred embodiments of the invention presented herein. Since numerous modifications and changes will occur to those skilled in the art, it is not desired to limit the invention to the exact construction used to illustrate the various means comprising this invention.

What is claimed is:

1. An article of manufacture, comprising a germicidal and disinfectant composition comprising a protease, an amylase, an enzyme stabilizing system, a detergent, and water, said germicidal and disinfectant composition being present in an absorbent material wipe and being able to reduce secondary infection said absorbent material wipe being attached to a disposable wiper having a re-sealable opening and being configured such that said absorbent material wipe can be disposed of without contacting a user's hands.

2. The article of manufacture of claim 1, wherein said secondary infection results from the presence of germs selected from the group consisting of HIV, hepatitis, smallpox, and anthrax.

3. The article of manufacture of claim 1, wherein said absorbent material wipe comprises a non-woven material.

4. The article of manufacture of claim 1, wherein said germicidal and disinfectant composition saturates the absorbent material wipe.

5. The article of manufacture of claim 1, wherein said germicidal and disinfectant composition is biodegradable.

6. The article of manufacture of claim 1, wherein the activity range of the protease is between pH 6.8 and 9.

7. The article of manufacture of claim 1, wherein the protease will function at temperatures of about 90 degrees C.

8. The article of manufacture of claim 1, wherein the activity range of the amylase is between pH 6.8 and 11.5.

9. The article of manufacture of claim 1, wherein the amylase will function at temperatures of about 90 degrees C.

10. The article of manufacture of claim 1, wherein lipase is included.

11. The article of manufacture of claim 1, wherein the combined concentration of the protease and the amylase is 0.1% by weight.

12. The article of manufacture of claim 1, wherein the activity of the protease and the amylase is between 80% and 90% after 8 weeks of storage.

13. The article of manufacture of claim 1, wherein the enzyme stabilizing system includes an alkanolamine, a calcium salt, and an alcohol.

14. The article of manufacture of claim 13, wherein the alkanolamine is triethanolamine.

15. The article of manufacture of claim 13, wherein the alcohol is selected from the group consisting of alkyl alcohols and branched alcohols.

16. The article of manufacture of claim 15, wherein the alkyl alcohol is selected from the group consisting of ethanol and isopropyl alcohol.

17. The article of manufacture of claim 13, wherein the alcohol is present at concentrations of up to 25% by weight.

18. The article of manufacture of claim 1, wherein the enzyme stabilizing system further includes a petroleum distillate.

19. The article of manufacture of claim 18, wherein the petroleum distillate is mineral spirits.

20. The article of manufacture of claim 18, wherein the petroleum distillate is present at concentrations of up to 75% by weight.

21. The article of manufacture of claim 1, wherein the detergent is nonionic.

22. The article of manufacture of claim 21, wherein the hydrophile/lipophile balance number of the nonionic detergent is between about 3 and about 15.

23. The article of manufacture of claim 21, wherein the nonionic detergent is selected from the group consisting of ethoxylated fatty alcohols and ethoxylated fatty acids represented by the generic formula $RA(CH_2CH_2O)_nH$ wherein R represents the hydrophobic moiety and has between 8 and 22 carbon atoms, A represents the group carrying the reactive hydrogen atom, and n represents the group average number of ethylene oxide moieties which is between 2 and 8.

24. The article of manufacture of claim 1, wherein the detergent is anionic.

25. The article of manufacture of claim 24, wherein the anionic detergent is represented by the general formula RSOM wherein R represents a hydrocarbon selected from the group consisting of straight or branched alkyl radicals containing from about 8 to about 24 carbon atoms, M is a salt forming cation which is selected from the group consisting of sodium, potassium, ammonium and derivatives thereof.

26. The article of manufacture of claim 24, wherein the anionic detergent is sodium laureth sulfate.

27. The article of manufacture of claim 1, wherein the water comprises between 40% and 50% of total weight.

28. The article of manufacture of claim 1, wherein said disposable wiper is in the form of a flexible bag having a re-sealable opening.

29. The article of manufacture of claim 1, wherein said absorbent material wipe is affixed to an inside surface of said disposable wiper, and further wherein said disposable wiper is adapted to allow partial eversion to expose said absorbent material wipe and thereby allow usage thereof.

30. The article of manufacture of claim 28, wherein the flexible bag is adapted to form a non-drip cuff around said absorbent material wipe with partial eversion of the flexible bag.

31. The article of manufacture of claim 30, wherein the flexible bag is adapted to form a reservoir for excess liquid as part of said non-drip cuff.

32. The article of manufacture of claim 30, wherein the flexible bag is adapted to allow insertion of a human hand to cause eversion and to enable usage of said disposable wiper after partial eversion.

33. The article of manufacture of claim 32, wherein said re-sealable opening is large enough to accommodate a human hand.

34. The article of manufacture of claim 30, wherein said flexible bag is a flat plastic bag having two opposing inside surfaces, and further wherein said absorbent material wipe has separate portions each affixed to a separate inside surface of said plastic bag.

35. The article of manufacture of claim 30, wherein said flexible bag includes instructions located on at least one outside surface and oriented to locate the re-sealable opening along a top edge with respect thereto.

36. An article of manufacture, comprising a germicidal and disinfectant composition comprising an aqueous solution of 0.05% calcium chloride; 2% sodium formate; 1% triethanolamine; 5% ethanol; 30% linear primary alcohol ethoxylate selected from the group consisting of ethoxylated fatty alcohols and ethoxylated fatty acids represented by the generic formula $RA(CH_2CH_2O)_nH$ wherein R represents the hydrophobic moiety and has between 8 and 22 carbon atoms, A represents the group carrying the reactive hydrogen atom, and n represents the group average number of ethylene oxide moieties which is between 2 and 8; 20% sodium laureth sulfate; and an enzyme solution having a concentration of between 0.2% and 3% by weight wherein the enzymes present are protease, lipase, and alpha-amylase; said germicidal and disinfectant composition being able to reduce secondary infection and being contained in a disposable wiper having an absorbent material wipe attached thereto that is wetted with said germicidal and disinfectant composition, said disposable wiper being configured such that said absorbent material wipe can be disposed of without contacting a user's hands.

37. The article of manufacture of claim 36, wherein said secondary infection results from the presence of germs selected from the group consisting of HIV, hepatitis, smallpox, and anthrax.

38. The article of manufacture of claim 36, wherein said absorbent material wipe comprises a non-woven material.

39. The article of manufacture of claim 36, wherein said germicidal and disinfectant composition saturates the absorbent material wipe.

40. The article of manufacture of claim 36, wherein said germicidal and disinfectant composition is biodegradable.

41. The article of manufacture of claim 36, wherein the activity range of the protease is between pH 6.8 and 9.

42. The article of manufacture of claim 36, wherein the protease will function at temperatures of about 90 degrees C.

43. The article of manufacture of claim 36, wherein the activity range of the amylase is between pH 6.8 and 11.5.

44. The article of manufacture of claim 36, wherein the amylase will function at temperatures of about 90 degrees C.

45. The article of manufacture of claim 28, wherein the activity of the protease and the amylase is between 80% and 90% after 8 weeks of storage.

46. The article of manufacture of claim 36, wherein the enzyme stabilizing system further includes a petroleum distillate.

47. The article of manufacture of claim 46, wherein the petroleum distillate is mineral spirits.

48. The article of manufacture of claim 46, wherein the petroleum distillate is present at concentrations of up to 75% by weight.

49. The article of manufacture of claim 36, wherein said disposable wiper comprises an flexible bag in which one can insert one's hand with one side of the flexible bag having the absorbent material wipe that will be wetted or soaked with the germicidal and disinfectant composition attached thereto.

50. An article of manufacture, comprising a germicidal and disinfectant composition comprising an aqueous solution of 20% linear alcohol ethoxylate selected from the group consisting of ethoxylated fatty alcohols and ethoxylated fatty acids represented by the generic formula $RA(CH_2CH_2O)_nH$ wherein R represents the hydrophobic moiety and has between 8 and 22 carbon atoms, A represents the group carrying the reactive hydrogen atom, and n represents the group average number of ethylene oxide moieties which is between 2 and 8; 20% mineral spirits; 12% isopropanol; about 1.2% triethanolamine; 2.3% oleic acid; 0.05% calcium chloride; 2% sodium formate; and an enzyme solution having a concentration of between 0.2% and 3% by weight wherein the enzymes present are protease, lipase, and alpha-amylase; said germicidal and disinfectant composition being able to reduce secondary infection and being contained in a disposable wiper having an absorbent material wipe attached thereto that is wetted with said germicidal and disinfectant composition, said disposable wiper being configured such that it can be disposed of without contacting a user's hands.

51. The article of manufacture of claim 50, wherein said secondary infection results from the presence of germs selected from the group consisting of HIV, hepatitis, smallpox, and anthrax.

52. The article of manufacture of claim 50, wherein said absorbent material wipe comprises a non-woven material.

53. The article of manufacture of claim 50, wherein said germicidal and disinfectant composition saturates the absorbent material wipe.

54. The article of manufacture of claim 50, wherein said germicidal and disinfectant composition is biodegradable.

55. The article of manufacture of claim 50, wherein the activity range of the protease is between pH 6.8 and 9.

56. The article of manufacture of claim 50, wherein the protease will function at temperatures of about 90 degrees C.

57. The article of manufacture of claim 50, wherein the activity range of the amylase is between pH 6.8 and 11.5.

58. The article of manufacture of claim 50, wherein the amylase will function at temperatures of about 90 degrees C.

59. The article of manufacture of claim 50, wherein the activity of the protease and the amylase is between 80% and 90% after 8 weeks of storage.

60. The article of manufacture of claim 50, wherein said disposable wiper comprises a re-sealable flexible bag in which one can insert one's hand with one side of the flexible bag having the absorbent material wipe that will be wetted or soaked with the germicidal and disinfectant composition attached thereto.

61. The article of manufacture of claim 50, further comprising a kit wherein said kit comprises a container for holding said composition, a disposable wiper having an absorbent material wipe attached thereto, said disposable wiper being pre-treated, with said composition, and a containment device for depositing used disposable wipers therein.

62. A method for treating fresh and dried blood and bodily fluids comprising:
(a) contacting said fresh and dried blood and bodily fluids with a germicidal and disinfectant composition adapted to cause lysis of glycoprotein in infectious agents;
(b) absorbing said germicidal and disinfectant composition along with said fresh and dried blood and bodily fluids by using absorbent wipe material affixed inside a re-sealable flexible bag; and
(c) resealing said flexible bag for disposal including said absorbent wipe material with absorbed germicidal and disinfectant composition and fresh and dried blood and bodily fluids.

63. The method of claim 62, further comprising storing said germicidal and disinfectant composition in said absorbent wipe material in, said re-sealable flexible bag prior to said step of contacting.

64. The method of claim 62, wherein said step of resealing includes un-everting and re-sealing said re-sealable flexible bag.

65. The method of claim 62, wherein said step of partially everting said flexible bag includes forming a non-drip cuff around the exposed absorbent wipe material.

66. The method of claim 65, wherein said step of absorbing said germicidal and disinfectant composition includes inserting a human hand into an everted portion of said flexible bag and wearing this partially everted, flexible bag as a mitt.

67. The method of claim 62, wherein said germicidal and disinfectant composition includes a protease, an amylase, an enzyme stabilizing system, a detergent, and water.

68. The method of claim 62, further comprising storing said germicidal and disinfectant composition and said absorbent wipe material in a biohazard clean-up kit prior to usage.

69. The method of claim 68, further comprising storing said germicidal and disinfectant composition in said biohazard kit in a sealed dispensing container.

70. The method of claim 68, containing said biohazard clean-up kit in a sealed, re-sealable bag adapted for use as a biohazard disposal bag.

71. The method of claim 70, further comprising storing protective gloves in said biohazard kit.

72. The method of claim 71, further comprising storing a biohazard disposal bag in said biohazard clean-up kit.

73. A germicidal and disinfectant composition comprising an aqueous solution of 0.05% calcium chloride; 2% sodium formate; 1% triethanolamine; 5% ethanol; 30% linear primary alcohol ethoxylate selected from the group consisting of ethoxylated fatty alcohols and ethoxylated fatty acids represented by the generic formula $RA(CH_2CH_2O)_nH$ wherein R represents the hydrophobic moiety and has between 8 and 22 carbon atoms, A represents the group carrying the reactive hydrogen atom, and n represents the group average number of ethylene oxide moieties which is between 2 and 8; 20% sodium laureth sulfate; and an enzyme solution having a concentration of between 0.2% and 3% by weight wherein the enzymes present are protease, lipase, and alpha-amylase; said germicidal and disinfectant composition being adapted to cause lysis of glycoprotein in infectious agents.

74. A germicidal and disinfectant composition comprising an aqueous solution of 20% linear alcohol ethoxylate selected from the group consisting of ethoxylated fatty alcohols and ethoxylated fatty acids represented by the generic formula $RA(CH_2CH_2O)_nH$ wherein R represents the hydrophobic moiety and has between 8 and 22 carbon atoms, A represents the group carrying the reactive hydrogen atom, and n represents the group average number of ethylene oxide moieties which is between 2 and 8; 20% mineral spirits; 12% isopropanol; about 1.2% triethanolamine; 2.3% oleic acid; 0.05% calcium chloride; 2% sodium formate; and an enzyme solution having a concentration of between 0.2% and 3% by weight wherein the enzymes present are protease, lipase, and alpha-amylase; said germicidal and disinfectant composition being adapted to cause lysis of glycoprotein in infectious agents.

75. A biohazard clean-up kit, comprising:
a germicidal and disinfectant composition including a protease, an amylase, an enzyme stabilizing system, a detergent, and water, said germicidal and disinfectant composition being adapted to cause lysis of glycoprotein in infectious agents; and
an absorbent material wipe affixed to a re-sealable flexible bag, wherein said flexible bag is adapted to function as a biohazard disposal container.

76. The biohazard clean-up kit of claim 75, wherein said biohazard disposal container is re-sealable and serves as a storage container for said absorbent material wipe and said germicidal and disinfectant composition.

77. The biohazard clean-up kit of claim 76, further comprising protective gloves.

78. The biohazard clean-up kit of claim 77, wherein said germicidal and disinfectant composition is stored in a sealed, dispensing container.

79. An article of manufacture, comprising a germicidal and disinfectant composition comprising a protease, an amylase, an enzyme stabilizing system, a detergent, and water, said germicidal and disinfectant composition being able to reduce secondary infection and being contained in a disposable wiper having an absorbent material wipe attached thereto that is wetted with said germicidal and disinfectant composition, said disposable wiper being configured such that said absorbent material wipe can be disposed of without contacting a user's hands and said disposable wiper including a re-sealable flexible bag having said absorbent material wipe affixed to an inside surface of said flexible bag, said flexible bag being adapted to allow partial eversion to expose said absorbent material wipe and thereby allow usage thereof.

80. The germicidal and disinfectant composition of claim 29, wherein said flexible bag is adapted to allow un-eversion and resealing after usage.

81. The method of claim 63, further comprising:

opening said sealed, re-sealable flexible bag; and partially everting said flexible bag to expose said absorbent wipe material to facilitate said step of contacting.

* * * * *

UNITED STATES PATENT AND TRADEMARK OFFICE
CERTIFICATE OF CORRECTION

PATENT NO. : 6,753,306 B2
DATED : June 22, 2004
INVENTOR(S) : Joseph J. Simpson

It is certified that error appears in the above-identified patent and that said Letters Patent is hereby corrected as shown below:

Column 10,
Line 30, "infection said" should read -- infection, said --; and

Column 13,
Line 66, "material in, said" should read -- material in said --.

Signed and Sealed this

Twenty-third Day of November, 2004

JON W. DUDAS
*Director of the United States Patent and Trademark Office*